US00PP20887P2

(12) United States Plant Patent
Traven et al.

(10) Patent No.: US PP20,887 P2
(45) Date of Patent: Mar. 23, 2010

(54) ***SOLENOSTEMON* PLANT NAMED 'WITCH DOCTOR'**

(50) Latin Name: *Solenostemon scutellarioides*
Varietal Denomination: Witch Doctor

(76) Inventors: Lloyd Traven, 295 Park Dr. West, Kintnersville, PA (US) 18930; Ralph J. Repp, 71 West End Cir., Waynesville, NC (US) 28785

( * ) Notice: Subject to any disclaimer, the term of this patent is extended or adjusted under 35 U.S.C. 154(b) by 0 days.

(21) Appl. No.: 12/291,554

(22) Filed: Nov. 12, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—Susan B McCormick Ewoldt
(74) *Attorney, Agent, or Firm*—C. A. Whealy

(57) ABSTRACT

A new and distinct cultivar of *Solenostemon* plant named 'Witch Doctor', characterized by its upright and mounded plant habit; freely branching habit; purple-colored stems; and deeply lobed green-colored leaves with dark purple-colored margins and venation.

1 Drawing Sheet

Botanical designation: *Solenostemon scutellarioides.*
Cultivar denomination: 'Witch Doctor'.

BACKGROUND OF THE INVENTION

The present invention relates to a new and distinct cultivar of *Solenostemon* plant, botanically known as *Solenostemon scutellarioides*, and hereinafter referred to by the name 'Witch Doctor'.

The new *Solenostemon* plant is a naturally-occurring whole plant mutation of *Solenostemon scutellarioides* 'Sparkler', not patented. The new *Solenostemon* plant was discovered and selected by the Inventors as a single plant from within a population of plants of 'Sparkler' in a controlled greenhouse environment in Kintnersville, Pa. in 2005.

Asexual reproduction of the new *Solenostemon* plant by tip cuttings in a controlled greenhouse environment in Kintnersville, Pa. since 2005, has shown that the unique features of this new *Solenostemon* plant are stable and reproduced true to type in successive generations.

SUMMARY OF THE INVENTION

Plants of the new *Solenostemon* have not been observed under all possible environmental conditions. The phenotype may vary somewhat with variations in environment such as temperature and light intensity, without, however, any variance in genotype.

The following traits have been repeatedly observed and are determined to be the unique characteristics of 'Witch Doctor'. These characteristics in combination distinguish 'Witch Doctor' as a new and distinct cultivar of *Solenostemon:*

1. Upright and mounded plant habit.
2. Freely branching habit.
3. Purple-colored stems.
4. Deeply lobed green-colored leaves with dark purple-colored margins and venation.

Plants of the new *Solenostemon* can be compared to plants of the parent, 'Sparkler'. Plants of the new *Solenostemon* differ from plants of 'Sparkler' in the following characteristics:

1. Plants of the new *Solenostemon* and 'Sparkler' differ in stem coloration as plants of 'Sparkler' have yellow green-colored stems.
2. Plants of the new *Solenostemon* and 'Sparkler' differ in leaf coloration as plants of 'Sparkler' have bright yellow-colored leaves with dark green-colored margins and red purple-colored markings.

Plants of the new *Solenostemon* can also be compared to plants of the *Solenostemon* 'Alligator', not patented. In side-by-side comparisons conducted in Kintnersville, Pa., plants of the new *Solenostemon* differed from plants of 'Alligator' in the following characteristics:

1. Plants of the new *Solenostemon* had deeply lobed leaves whereas plants of 'Alligator' had leaves with scalloped margins.
2. Plants of the new *Solenostemon* and 'Alligator' differed in leaf color as plants of 'Alligator' had very dark green-colored leaves with variable cream, yellow, purple, and red markings.

BRIEF DESCRIPTION OF THE PHOTOGRAPHS

The accompanying colored photographs illustrate the overall appearance of the new *Solenostemon* plant, showing the colors as true as it is reasonably possible to obtain in colored reproductions of this type. Colors in the photographs may differ slightly from the color values cited in the detailed botanical description which accurately describe the colors of the new *Solenostemon*.

The photograph at the bottom of the sheet comprises a side perspective view of a typical plant of 'Witch Doctor' grown in a container.

The photograph at the top of the sheet is a close-up view of typical leaves of 'Witch Doctor'.

DETAILED BOTANICAL DESCRIPTIONS

Plants used for the aforementioned photographs and following observations and measurements were grown in Encinitas, Calif. during the spring in a polyethylene-covered greenhouse and under commercial production conditions During the production of the plants, day temperatures averaged 24° C., night temperatures averaged 16° C. and light levels averaged 4,000 foot-candles. Plants had been growing for 13 weeks when the photographs and the description were taken. In the following description, color references are made to The Royal Horticultural Society Colour Chart, 2001 Edition, except where general terms of ordinary dictionary significance are used.

Botanical classification: *Solenostemon scutellarioides* 'Witch Doctor'.

Parentage: Naturally-occurring whole plant mutation of *Solenostemon scutellarioides* 'Sparkler', not patented.

Propagation:

*Type.*—By tip cuttings.

*Time to initiate roots, summer.*—About six days at temperatures of about 29° C.

*Time to initiate roots, winter.*—About seven to eight days at temperatures of about 18° C.

*Time to produce a rooted young plant, summer.*—About 14 to 16 days at temperatures of about 29° C.

*Time to produce a rooted young plant, winter.*—About 18 to 20 days at temperatures of about 18° C.

*Root description.*—Medium in thickness, fibrous; white in color.

*Rooting habit.*—Freely branching; moderately dense.

Plant description:

*Plant form and growth habit.*—Compact and mounded plant habit; freely branching habit with about seven to eight primary branches per plant; primary branches with secondary branches at potentially every node; vigorous growth habit and moderate to fast growth rate.

*Plant height.*—About 17 cm.

*Plant width.*—About 25 cm.

*Branch description.*—Length: About 19 cm. Diameter: About 6 mm. Internode length: About 3.8 cm. Texture: Pubescent; longitudinally ridged. Color: Close to 187A.

*Leaf description.*—Arrangement: Opposite, simple. Length: About 6.4 cm. Width: About 6.2 cm. Shape: Roughly ovate; deeply lobed. Apex: Acute. Base: Attenuate. Margin: Deeply lobed. Texture, upper and lower surfaces: Surfaces, smooth, glabrous; margins, sparsely pubescent; surfaces rugose with prominent venation. Venation pattern: Pinnate; reticulate. Color: Developing leaves, upper surface: Close to 146B; margins and venation, close to N92A. Developing leaves, lower surface: Close to 187A. Fully expanded leaves, upper surface: Close to 146A; margins, close to N92A; venation, close to 146D or 187B. Fully expanded leaves, lower surface: Close to 146C to 146D; venation, close to 146D or 187A. Petioles: Length: About 2.4 cm. Diameter: About 2 mm. Texture, upper and lower surfaces: Scattered pubescence. Color, upper surface: Close to 187A. Color, lower surface: Close to N92A.

Flower description: Flower development has not been observed on plants of the new *Solenostemon*.

Disease/pest resistance: Resistance to pathogens and pests common to *Solenostemon* has not been observed.

Temperature tolerance: Plants of the new *Solenostemon* have been observed to tolerate temperatures from about 2° C. to about 35° C.

It is claimed:

1. A new and distinct *Solenostemon* plant named 'Witch Doctor' as illustrated and described.

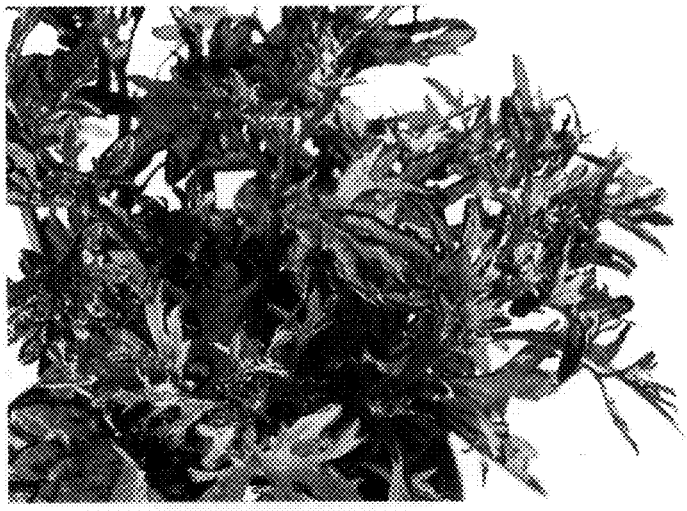
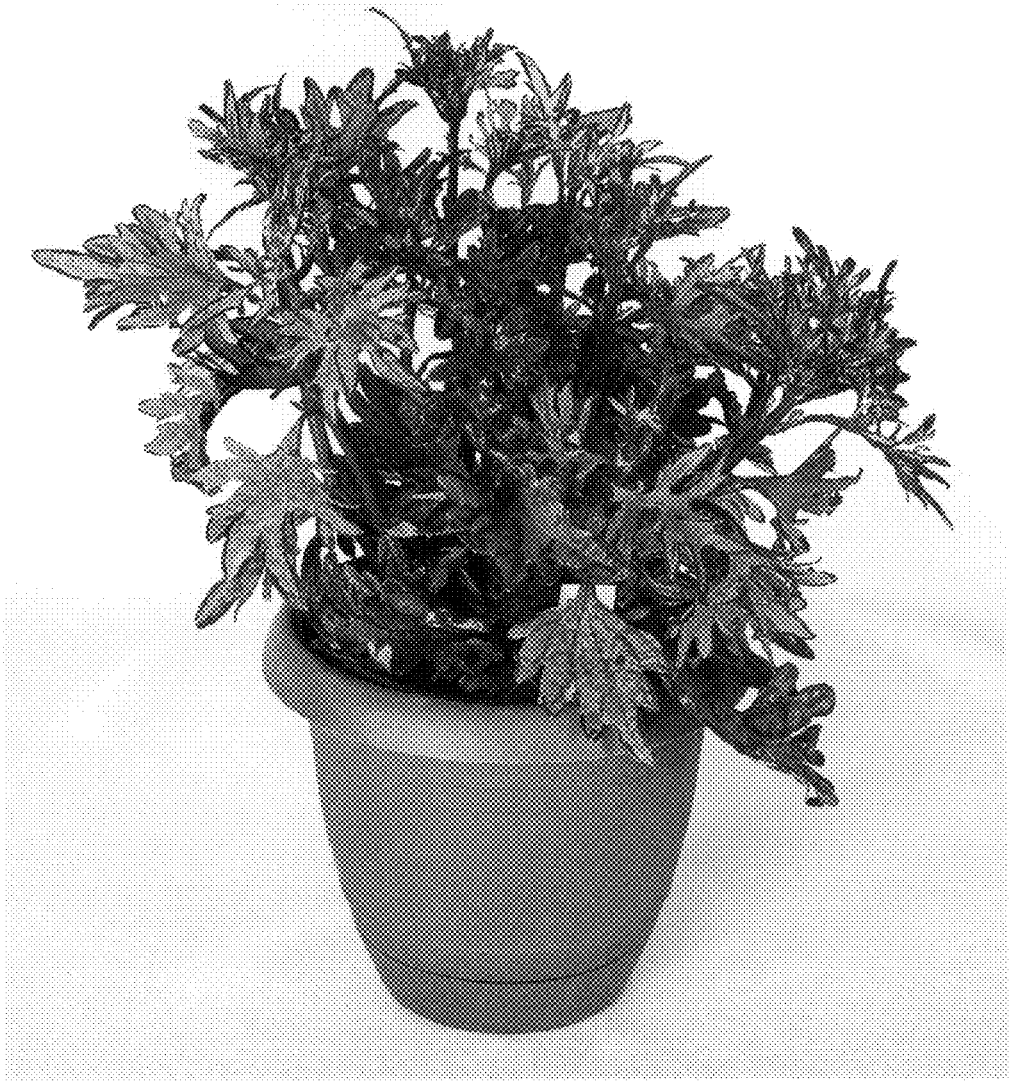

* * * * *